United States Patent
Thursby et al.

(10) Patent No.: US 10,133,055 B2
(45) Date of Patent: *Nov. 20, 2018

(54) OPTICAL ELEMENT

(71) Applicant: E.V. Offshore Limited, Norwich, Norfolk (GB)

(72) Inventors: Jonathan Thursby, Norwich (GB); Shaun Peck, Norwich (GB); Matthew Gibson-Ford, Norwich (GB)

(73) Assignee: E.V. OFFSHORE LIMITED, Norfolk (GB)

( * ) Notice: Subject to any disclaimer, the term of this patent is extended or adjusted under 35 U.S.C. 154(b) by 164 days.

This patent is subject to a terminal disclaimer.

(21) Appl. No.: 14/584,106

(22) Filed: Dec. 29, 2014

(65) Prior Publication Data

US 2015/0109433 A1 Apr. 23, 2015
US 2017/0242238 A9 Aug. 24, 2017

Related U.S. Application Data

(63) Continuation of application No. 13/884,109, filed as application No. PCT/GB2011/052185 on Nov. 10, 2011, now Pat. No. 8,979,401.

(30) Foreign Application Priority Data

Nov. 19, 2010 (GB) .................................. 1019642.6

(51) Int. Cl.
| | |
|---|---|
| *G03B 17/00* | (2006.01) |
| *G02B 17/00* | (2006.01) |
| *G02B 23/24* | (2006.01) |
| *G02B 1/02* | (2006.01) |
| *H04N 5/225* | (2006.01) |
| *E21B 47/00* | (2012.01) |

(52) U.S. Cl.
CPC ...... *G02B 23/2461* (2013.01); *E21B 47/0002* (2013.01); *G02B 1/02* (2013.01); *G02B 23/2446* (2013.01); *H04N 5/2256* (2013.01); *H04N 2005/2255* (2013.01)

(58) Field of Classification Search
USPC ............................................ 396/17, 19, 448
See application file for complete search history.

(56) References Cited

U.S. PATENT DOCUMENTS

| | | | | |
|---|---|---|---|---|
| 4,612,259 | A * | 9/1986 | Ueda ............................ | 428/661 |
| 6,627,866 | B2 * | 9/2003 | Hula et al. ................. | 250/208.1 |

(Continued)

FOREIGN PATENT DOCUMENTS

WO WO2012/066309 * 5/2012

*Primary Examiner* — Minh Q Phan
(74) *Attorney, Agent, or Firm* — Hayes Soloway PC

(57) ABSTRACT

The present invention relates to an optical element for use in a camera system for the inspection of passageways, a camera system for the inspection of passageways and a method of illuminating a passageway during inspection with a camera. An optical element for use in a camera system for the inspection of passageways comprises a first optical portion arranged to transmit light into a camera, a second optical portion arranged to transmit light emitted from a light source, the second optical portion located adjacent the first optical portion, and barrier means arranged to prevent light being transmitted from the second optical portion into the first optical portion.

18 Claims, 4 Drawing Sheets

(56) References Cited

U.S. PATENT DOCUMENTS

| | | | |
|---|---|---|---|
| 2008/0266445 A1* | 10/2008 | Park | 348/370 |
| 2010/0013984 A1* | 1/2010 | Loiacono | 348/373 |
| 2010/0033563 A1* | 2/2010 | Boehnlein et al. | 348/84 |
| 2011/0255000 A1* | 10/2011 | Weber | G03B 17/02 348/374 |
| 2012/0027399 A1* | 2/2012 | Yeates | 396/535 |

* cited by examiner

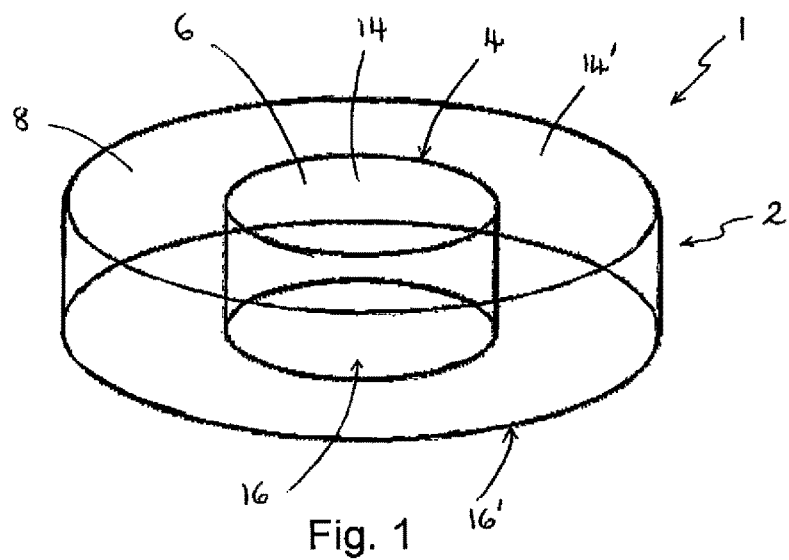
Fig. 1
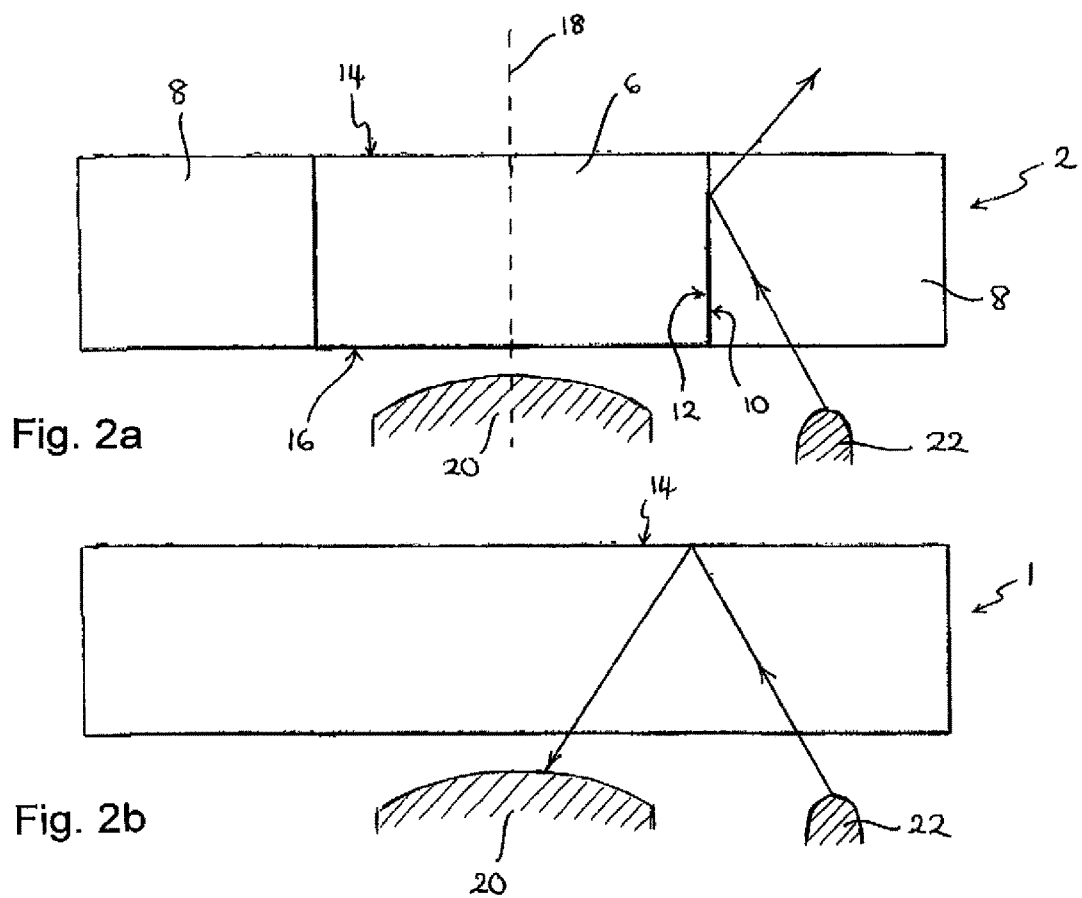
Fig. 2a
Fig. 2b

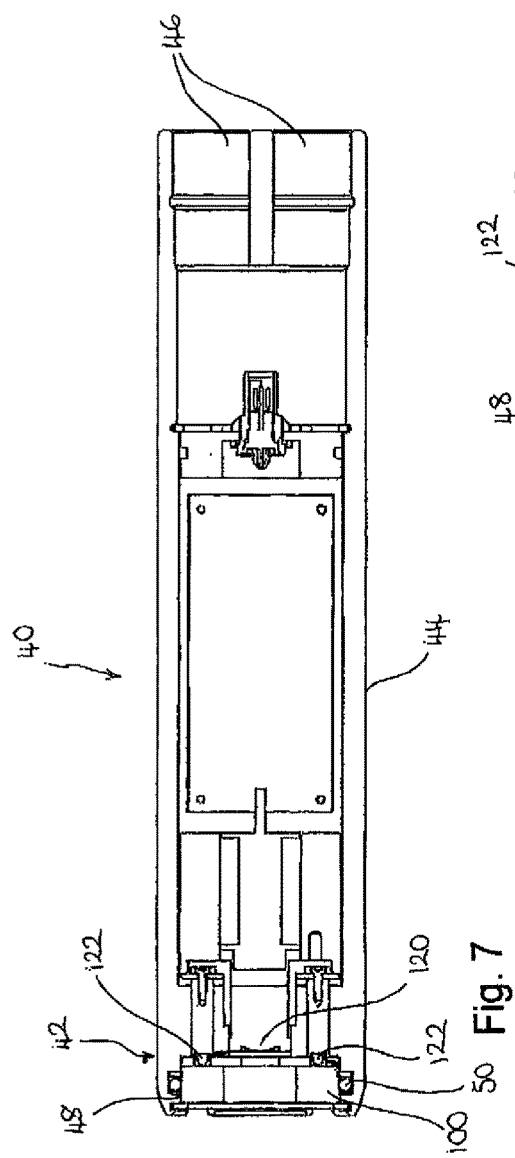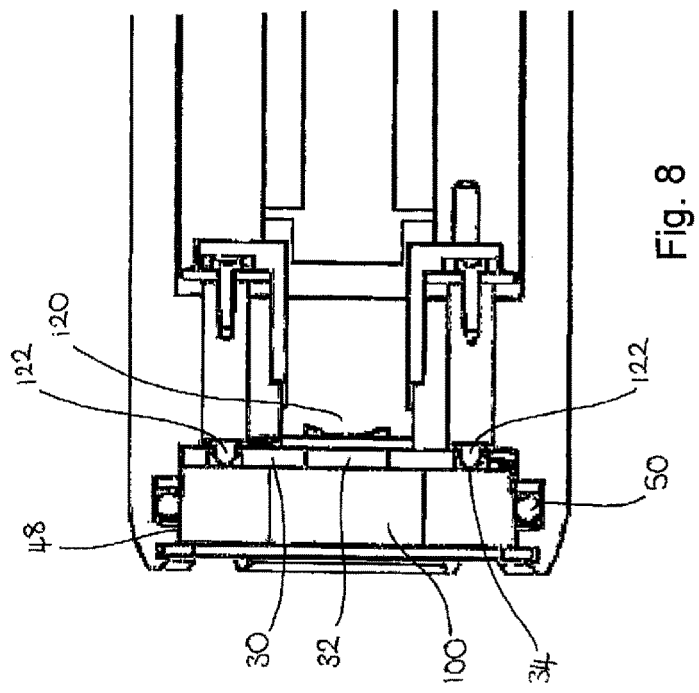

OPTICAL ELEMENT

CROSS-REFERENCE

This application is a continuation of application Ser. No. 13/884,109, now U.S. Pat. No. 8,979,401, having a 371(c) filing date of Nov. 10, 2011.

FIELD

The present invention relates to an optical element for use in a camera system for the inspection of passageways, a camera system for the inspection of passageways and a method of illuminating a passageway during inspection with a camera. In particular the invention relates to an optical element for protecting the video camera and the light source of a wellbore inspection system while permitting good illumination of the field of view of the camera.

BACKGROUND

In oil and gas wells, the wellbore may be open or may be clad with a well casing. Visual inspection of the wellbore is important, to check the integrity of the wellbore, and to investigate any downhole problems that may delay or prevent use of the well. For example, it is important to regularly inspect the casings for corrosion and wear.

Although visual inspection of the wellbore is important, the conditions typically found in a wellbore tend to hinder the ability to use many camera systems. Wellbores can have diameters in the range 10 centimeters to 1 meter and can reach depths of hundreds or thousands of meters. In order to inspect these bores, therefore, it is not only necessary to provide a camera system that can operate at these depths, but also to provide the lighting required to be able to capture still images or video in this confined environment.

Furthermore, any camera system must be able to withstand the pressures and temperatures encountered at depth in a borehole. Pressures at these depths can be very large and can reach around 150 MPa, and in addition, temperatures may exceed 100.degree. C.

Typically, downhole camera systems comprise a camera and light source contained in a protective steel sheath. These camera systems are lowered into the wellbore on an electrical cable or a shaft, with the images from the camera being relayed back to the surface where they are displayed and recorded.

The confined environment of the wellbore causes problems in designing a camera and lighting arrangement that is small enough while still delivering high enough light levels to capture the required images.

Several camera systems use a backlight system in which the light source is mounted at a distance behind the camera. The light is then directed into the field of view of the camera by means of a reflector mounted adjacent to the camera. However, this approach is less successful in narrower passageways as the size of the camera becomes too large compared to the diameter of the bore to allow sufficient light to be reflected.

It is also known to provide an array of light emitting diodes (LEDs) as the light source due to their relatively low power consumption and small size. These LEDs are typically mounted around the outside of the camera approximately level with the camera lens. The LEDs therefore directly illuminate the field of view of the camera.

In order to protect the camera and the light source from the harsh environment of the wellbore, a cover or window is typically placed over the distal end of the camera system. Any light emitted from the light source, therefore, must pass through this window before it illuminates the wellbore.

This has a disadvantage, however, because some of the light that travels through the window is internally reflected and does not pass through the window.

Furthermore, some of the internally reflected light is directed back towards the lens of the camera, leading to poor images.

It is an object of the present invention to provide an improved window for a subsea camera system that overcomes these problems.

SUMMARY OF THE INVENTION

According to the invention, there is provided an optical element for use in a camera system for the inspection of passageways, the element comprising: a first optical portion arranged to transmit light into a camera; a second optical portion arranged to transmit light emitted from a light source, the second optical portion located adjacent the first optical portion; and barrier means arranged to prevent light being transmitted from the second optical portion into the first optical portion.

Also according to the invention, there is provided a camera system for use in the inspection of passageways, the system comprising: a housing having opposing first and second ends; a camera mounted in the housing, the camera positioned proximate the first end of the housing; a light source arranged to direct emitted light out of the first end of the housing; and an optical element mounted at the first end of the housing, the element comprising: a first optical portion arranged to transmit light into the camera; a second optical portion arranged to transmit light emitted from the light source, the second optical portion located adjacent the first optical portion; and barrier means arranged to prevent light being transmitted from the second optical portion into the first optical portion.

Also according to the invention, there is provided a method of illuminating a passageway during inspection with a camera system, the camera system being according to the invention, and the method comprising the steps of:
  illuminating the light source to provide emitted light;
  transmitting the emitted light through the second optical portion in a first direction to illuminate an object; and
  transmitting light through the first optical portion in a second direction, substantially opposite to the first direction, into the camera so that the camera captures the image of the object;
  wherein, in use, the emitted light is prevented from being transmitted directly into the first optical portion from the second optical portion by said barrier means.

Preferably, the barrier means comprises reflecting means to reflect light in the second optical portion and to prevent light from the second optical portion being transmitted into the first optical portion. The reflecting means may comprise a reflecting surface, which may comprise a peripheral surface of the first optical portion and/or the second optical portion.

In a preferred embodiment the barrier means comprises an interface between the first optical portion and the second optical portion. The interface may be formed by an unpolished surface of at least one of the first and second optical portions.

In other embodiments, the barrier means comprises a gap between the first optical portion and the second optical portion. Preferably the gap is filled with silicone.

Preferably, the second optical portion surrounds the first optical portion. The first and second optical portions may be concentric. Preferably, the first optical portion is cylindrical and the second optical portion is annular and surrounds the first optical portion.

Preferably, the first and second optical portions are made of sapphire. However, the first and second optical portions may be made of any other suitable materials.

Preferably the optical portions are made of a ceramic material. More preferably the optical portions are made of quartz, diamond or crystal.

The optical element may be disc-shaped having parallel opposing first and second end faces and the barrier means may be substantially perpendicular to the first and second end faces.

In preferred embodiments, the optical element further comprises a base plate attached to the second end face. Preferably, the base plate is made of titanium and the first and second optical portions are bonded to the base plate by diffusion bonding.

When the optical element is mounted in a camera system, preferably the first end face of the optical element is closer to the first end of the housing than the second end face, and the camera and the light source are located adjacent to the second end face.

Preferably the light source is arranged, in use, to illuminate an object, the image of which is being captured by the camera.

Preferably, the camera system comprises a plurality of light sources. The plurality of light sources may comprise light emitting diodes.

Preferably, the plurality of light sources are arranged in a circle around the camera.

In embodiments in which the optical element comprises a base plate in contact with the second end face, preferably the base plate includes at least two apertures, and the camera and the light source are arranged so that at least a part of each of the camera and the light source are located within an aperture.

Preferably the second optical portion is arranged to transmit light from the light source in a first direction through the optical element. Preferably the first optical portion is arranged to transmit light into the camera in a second direction through the optical element. Preferably the first direction is the opposite direction to the second direction.

The barrier means may prevent light from the second optical portion travelling in the second direction being transmitted into the first optical portion.

Preferably the reflection means substantially maintains the light from the light source within the second optical portion as the light is transmitted from a second end of the second optical portion to a first end of the second optical portion.

Preferably the second optical portion extends from a first end face of the optical element to a second end face of the optical element and transmits light from the second end to the first end. Preferably the first optical portion extends from a first end face of the optical element to a second end face of the optical element and the camera receives light entering from the first end and which is transmitted to the second end of the optical element.

Preferably, the barrier means reflects light in the second optical portion and prevent light from the second optical portion being transmitted into the first optical portion. The barrier means may comprise a shroud. The shroud may locate around an outer peripheral surface of the first optical portion and/or an inner peripheral surface of the second optical portion.

BRIEF DESCRIPTION OF THE DRAWINGS

The invention will now be further described, by way of example only, and with reference to the accompanying drawings, in which:

FIG. 1 is a perspective view of an optical element for use in a camera system according to a first embodiment of the invention;

FIG. 2*a* is a schematic diagram illustrating light reflection by an interface present in the optical element of FIG. 1;

FIG. 2*b* is a schematic diagram illustrating internal light reflection by a front surface of an optical element when an interface is not present;

FIG. 7 is a cross-sectional view of a camera system including the optical element of FIG. 3; and FIG. 8 is an enlarged view of the front end of the camera system of FIG. 7, showing the arrangement of the camera lens, light sources and optical element.

DETAILED DESCRIPTION

Figure 3:
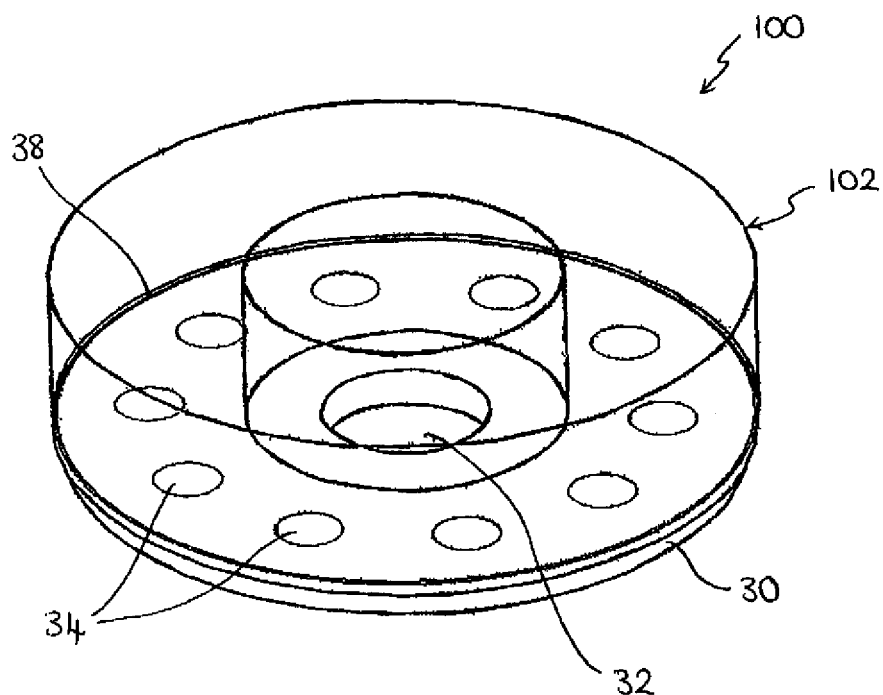
FIG. 3 is a perspective view of an optical element for use in a camera system according to a second preferred embodiment of the invention.

FIG. 1 shows a window or optical element 1 for use in a camera system that may be used to inspect wellbores or other passageways. These camera systems typically include a camera and one or more light sources arranged to light the field of view of the camera. Typically these are housed in a front, distal end region of an elongate cylindrical housing which is lowered down the wellbore by cables or a shaft attached at a second end. In most cases, the camera systems will also include a viewport or optical element at the front end of the camera housing that serves to protect the camera, in the harsh environmental of a wellbore for example.

In this embodiment the optical element 1 of the present invention comprises an optical layer 2 which includes an interface 4 which prevents light emitted from a light source being internally reflected within the optical element 1 back towards the camera.

The optical element 1 comprises a disc-shaped optical layer 2, which has a first, inner optical portion 6 and a second, outer optical portion 8. The inner portion 6 is cylindrical, and the ring-shaped outer portion 8 surrounds it so that an inner surface 10 of the outer portion 8 is substantially in contact with the outer surface 12 of the inner portion 6 thereby forming a cylindrical interface 4 between the inner and outer portions 6, 8.

The thickness of the inner and outer portions 6, 8 is the same so that the front and rear faces 14, 16 of the inner portion 6 are co-planar with the respective front and rear faces 14', 16' of the outer portion 8.

Preferably, both the inner and outer portions 6, 8 of the optical layer 2 are made of sapphire, however, the optical layer 2 may be made of quartz, diamond, crystal or any other suitable material. The material of the optical layer 2 must be optically clear, for example transparent or translucent, and must also be able to withstand the harsh conditions within a wellbore. For example, the optical layer must be able to withstand high pressures of over 100 MPa as well as high temperatures of up to around 200.degree. C. The material should also be able to withstand any corrosive chemicals that are encountered in the wellbore.

In a simplest embodiment the cylindrical interface 4 extends for the full thickness of the optical layer 2 and the plane of the interface 4 is substantially perpendicular to the front and rear faces 14, 16 of the layer 2. The inner and outer surfaces 10, 12 are unpolished so as to create a more optically reflective interface. When the optical element 1 is installed within a camera system as described above, light entering a camera 20 is transmitted predominantly through the inner optical portion 6, and the light emitted by light sources 22 is transmitted substantially through the outer optical portion 8. Due to the nature of the interface 4, emitted light travelling in a range of angles towards the central axis 18 of the apparatus is reflected by the interface 4 and is directed outwards, away from the central axis 18. This is shown most clearly in FIG. 2a. If the interface 4 was not present, then emitted light travelling in the same direction, as shown in FIG. 2b, would be reflected from the front surface 14 of the optical element 1 back towards the camera.

The presence of the interface 4, therefore, has two important advantages. Emitted light that would otherwise be internally reflected towards the camera is now reflected outwards through the front face 14 of outer portion 8 of the optical element 1. This means that, firstly, more light is available to illuminate the field of view of the camera, and in particular the walls of the wellbore passageway, and secondly emitted light is prevented from being internally reflected into the camera which would otherwise adversely affect picture quality.

FIG. 3 shows a second preferred embodiment of an optical element 100. In this example, the optical layer 102 is mounted on a base layer or base plate 30. The base plate 30 is disc-shaped and has an outer diameter equal to the outer diameter of the optical layer 102. The thickness of the base plate 30 is significantly less than the thickness of the optical layer 102, and in this embodiment the base plate 30 is about one quarter of the thickness of the optical layer 102.

The base plate 30 supports the optical layer 102 and includes a plurality of apertures 32,34 for receiving other parts of the camera system, as will be described in more detail below. In this example, the base plate 30 is made of titanium, however, the base plate may be made of any other suitable metallic material. Of importance in the selection of material for the base plate 30 is the matching of the coefficients of thermal expansion of the materials of the base plate 30 and the optical layer 102. This is important as the optical element will be subjected to a large range of temperatures in use, for example −40.degree. C. to 200.degree. C., and a mismatch of coefficients of thermal expansion may lead to cracking or at least de-bonding of the optical layer 102.

The base plate 30 and the optical layer 102 are bonded together so that the rear face 116 of the optical layer 102 is in intimate contact with a front face 36 of the base plate 30. In particular, in a preferred embodiment, a sapphire optical layer 102 is bonded to a titanium base plate 30 by a process known as diffusion bonding. This process uses high compressive forces and heat to bond the two materials at an atomic level. Preferably, a layer of aluminium 38 is introduced between the optical layer 102 and the base plate 30 to act as a 'glue' and aid in the diffusion bonding process. Other soft metals may be used to form the bond layer, however, the bond layer must be compliant.

Figure 5:
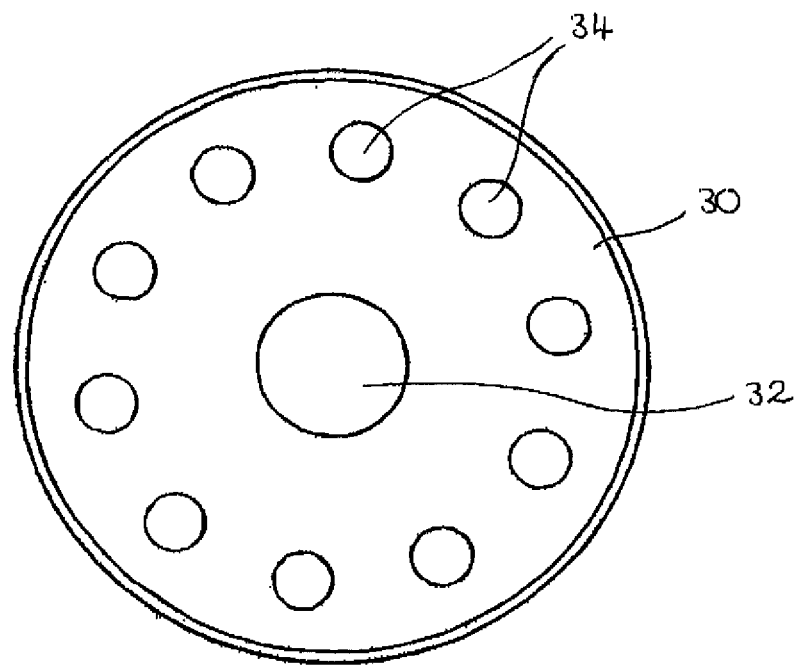
FIG. 5 is a rear view of the optical element of FIG. 3 showing the arrangement of apertures in the base plate.

The base plate 30 includes a larger central aperture 32 and several smaller apertures 34 arranged in a circle around the central aperture 32, as shown most clearly in FIG. 5. The smaller apertures 34 are spaced equidistantly around the circle and in this example there are ten apertures 34. The central aperture 32 is sized to receive a lens of a camera that is mounted behind the base plate 30 when the optical element is installed in a camera system, and the smaller apertures 34 are designed to each house a single one of a number of light sources that are arranged to emit light to illuminate the field of view of the camera.

Figure 4:
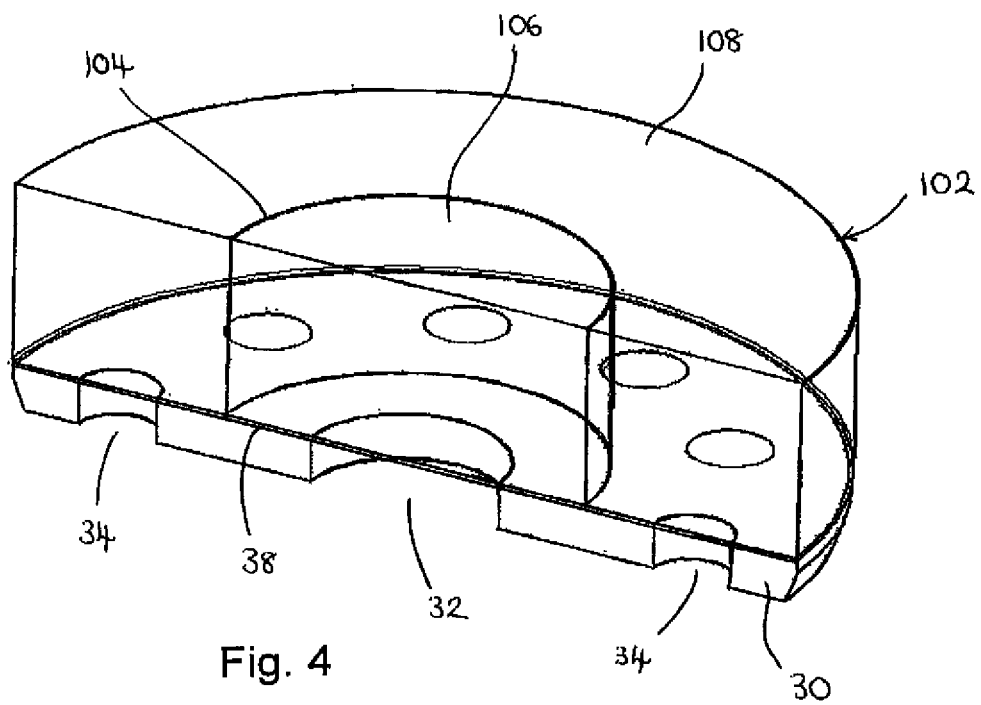
FIG. 4 is a sectional view of the optical element of FIG. 3.

The dimensions of the inner and outer portions 106, 108 of the optical layer 102 are such that the central aperture 32 is aligned with the inner portion 106 and the outer apertures 34 are aligned with the outer portion 108 so that the interface 104 between the portions lies between the central aperture 32 and the outer circle of apertures 34, as shown most clearly in FIG. 4.

Figure 6:
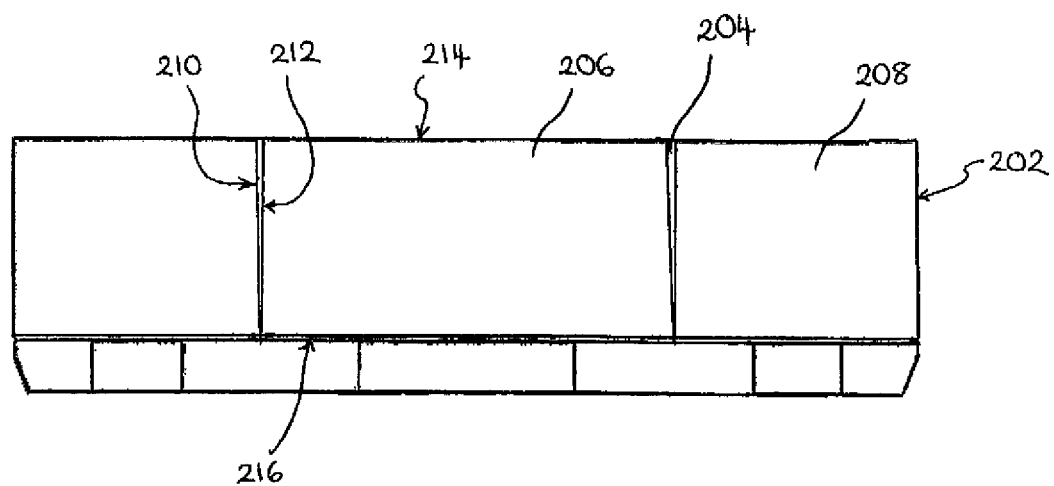
FIG. 6 is a cross-sectional view of the optical element of FIG. 3 with the gap between the first and second optical portions exaggerated.

As shown in FIG. 6, in another preferred embodiment, the interface 204 is in the form of a tapered annular gap 204 between the inner and outer optical portions 206, 208. This tapered gap 204 is such that the outer surface 212 of the inner portion 206 and the inner surface 210 of the outer portion 208 are in contact at the rear face 216 of the optical layer 202, but are spaced apart at the front face 214. The size of the gap 204 shown in FIG. 6 is exaggerated and typically the gap is minimal and primarily due to manufacturing tolerances between the inner and outer portions 206, 208 of the optical layer 202.

The gap 204 is filled with silicone which is preferably aerospace grade. In other embodiments other fillers may be used such as other grades of silicone, epoxies, rubbers or adhesives. Typically the choice of filler will be dependent on the environment in which the optical element will be used. The gap 204 must be filled to prevent contamination reaching the bond between the optical layer 202 and the base plate 230. This is particularly important when aluminium is used to aid the bonding process due to the relatively reactive nature of aluminium with many different chemicals.

Further, in a preferred embodiment, the inner and outer surfaces 210, 212 forming the interface 204 include a vapour deposition surface coating. This roughens the surfaces, further increasing the reflective nature of the interface 204.

In other embodiments, the inner and outer surfaces 210, 212 forming the interface 204 may be processed or treated in some other way to increase the reflective nature of the interface 204. For example, one or both of the surfaces 210, 212 may be painted, or the surfaces may be textured by a process other than vapour deposition.

FIGS. 7 and 8 show the optical element 100 in place in the distal end 42 of a camera system 40. The camera system 40 comprises a cylindrical housing 44 which is typically made of stainless steel to withstand the operating environment at depth in a wellbore. In addition to the camera 120 and light sources 122, the camera system 40 may also include a power supply, data transmitters and receivers, and controllers for controlling the camera 120 and light sources 122.

Connectors 46 are located at one end of the cylindrical camera system 40 for connecting to cables or a shaft used to lower the camera 40 down a wellbore and also for permitting electrical connections to be made to transmit data back up to the surface.

The optical element 100 is located in a recess 48 in the distal end 42 of the housing 44 at the opposite end to the connectors 46.

The camera is mounted directly behind the base plate 30 of the optical element 100 such that the lens of the camera 120 is aligned with the central aperture 32 in the base plate 30. The light sources 122, which in this embodiment are light emitting diodes (LEDs) 122, protrude through the smaller apertures 34 such that at least a front portion of the LEDs 122 are within the base plate 30, as shown most clearly in FIG. 8.

An O-ring 50 is used to form a seal between the optical layer 102 of the optical element 100 and the internal surface of the housing 44. The use of a single optical element 100 having distinct inner and outer portions within an optical layer bonded to a unitary base plate means that only a single high pressure seal is required to seal the entire optical element 100 in the end of the camera system 40. If the two optical portions were provided by two separate optical elements, or if the optical layer was not securely bonded to the base plate, then a number of high pressure seals would be required within the camera system to provide effective seals around each of the components. This would take up valuable space within the camera system and would decrease the available field of view of the camera.

Although in the above-described embodiments the optical layer is disc-shaped and comprises concentric inner and outer optical portions the optical layer may be of any suitable shape for use within a camera system. Furthermore, the second optical portion may not surround the first optical portion but, instead, the first and second optical portions may be located side by side or in any other relative positions depending on the corresponding relative positions of the camera and light sources in the camera system.

The optical element of the present invention, therefore, provides an improvement over existing camera system viewports by preventing unwanted internal reflections while maximising the illumination provided by the light sources and maximising the available field of view of the camera.

The invention claimed is:

1. An optical element for use in a camera system for the inspection of wellbore passageways, the element comprising an optical layer having opposing first and second solid end faces, and the optical layer comprising:
    a first optical portion comprising a first optically clear material arranged to transmit light into a camera, said first optical portion having opposing front and rear faces; and
    a second optical portion comprising a second optically clear material arranged to transmit light emitted from a light source, said second optical portion located adjacent said first optical portion and said second optical portion having opposing front and rear faces, the front faces of the first and second optical portions being co-planar and forming said first end face of the optical layer, and the rear faces of the first and second optical portions being co-planar and forming said second end face of the optical layer,
    wherein the first optical portion and the second optical portion are separate and distinct, and
    wherein at least a portion of a surface of said second optically clear material of said second optical portion is in direct and abutting contact with at least a portion of a surface of said first optically clear material of said first optical portion, and barrier means between said first and second optical portions comprises an interface formed by said contact, the barrier means being arranged to prevent light being transmitted from said second optical portion into said first optical portion.

2. An optical element as claimed in claim 1, wherein said barrier means comprises a peripheral surface of said first optical portion and/or said second optical portion arranged to reflect light in the second optical portion and to prevent light from the second optical portion being transmitted into the first optical portion.

3. An optical element as claimed in claim 1, wherein said interface is formed by an unpolished surface of at least one of said first and second optical portions.

4. An optical element as claimed in claim 1, wherein said second optical portion surrounds said first optical portion.

5. An optical element as claimed in claim 1, wherein said first and second optical portions are concentric.

6. An optical element as claimed in claim 1, wherein said first optical portion is cylindrical and said second optical portion is annular and surrounds said first optical portion.

7. An optical element as claimed in claim 1, wherein said first and second optical materials are sapphire, quartz, diamond or crystal.

8. An optical element as claimed in claim 1, wherein said barrier means is substantially perpendicular to said first and second end faces.

9. An optical element as claimed in claim 1, wherein the optical element further comprises a base plate attached to said second end face.

10. An optical element as claimed in claim 9, wherein the base plate includes a plurality of apertures.

11. An optical element as claimed in claim 9, wherein said base plate is made of titanium and said first and second optical portions are bonded to the base plate by diffusion bonding.

12. An optical element as claimed in claim 1, wherein said first optical portion consists of the first optically clear material and said second optical portion consists of the second optically clear material.

13. A camera system for use in the inspection of wellbore passageways, the system comprising:
    a housing having opposing first and second ends;
    a camera mounted in said housing, said camera positioned proximate said first end of said housing;
    a light source arranged to direct emitted light out of said first end of said housing; and
    an optical element mounted at said first end of said housing, said element comprising an optical layer having opposing first and second solid end faces, and the optical layer comprising:
    a first optical portion comprising a first optically clear material arranged to transmit light into said camera, the first optical portion having opposing front and rear faces;
    a second optical portion comprising a second optically clear material arranged to transmit light emitted from said light source, said second optical portion located adjacent said first optical portion and said second optical portion having opposing front and rear faces, the front faces of the first and second optical portions being co-planar and forming said first end face of the optical layer, and the rear faces of the first and second optical portions being co-planar and forming said second end face of the optical layer; and
    wherein the first optical portion and the second optical portion are separate and distinct and wherein at least a portion of a surface of said second optically clear material of said second optical portion is in direct and abutting contact with at least a portion of a surface of said first optically clear material of said first optical portion, and barrier means between said first and second optical portions comprises an interface formed by said contact, the barrier means being arranged to prevent light being transmitted from said second optical portion into said first optical portion.

14. A camera system as claimed in claim 13, wherein:
said first end face is closer to the first end of said housing than said second end face; and
said camera and said light source are located adjacent to the second end face.

15. A camera system as claimed in claim 13, wherein the camera system comprises a plurality of light sources.

16. A camera system as claimed in claim 15, wherein said plurality of light sources comprises light emitting diodes.

17. A camera system as claimed in claim 13, wherein the optical element comprises a base plate in contact with said second end face, the base plate including at least two apertures, and said camera and said light source are arranged so that at least a part of each of said camera and said light source are located within an aperture.

18. A method of illuminating a wellbore passageway during inspection with a camera system, the camera system being as claimed in claim 13, and the method comprising the steps of:
illuminating said light source to provide emitted light;
transmitting said emitted light through said second optical portion in a first direction to illuminate an object; and
transmitting light through said first optical portion in a second direction, substantially opposite to said first direction, into said camera so that said camera captures the image of said object;
wherein, in use, the emitted light is prevented from being transmitted directly into said first optical portion from said second optical portion by said barrier means.

* * * * *